US007655602B2

(12) United States Patent
Anderson

(10) Patent No.: US 7,655,602 B2
(45) Date of Patent: Feb. 2, 2010

(54) PEPTIDES COMPRISING AROMATIC D-AMINO ACIDS AND METHODS OF USE

(75) Inventor: Byron E. Anderson, Morton Grove, IL (US)

(73) Assignee: Bio Science International, Inc., Germantown, WI (US)

( * ) Notice: Subject to any disclaimer, the term of this patent is extended or adjusted under 35 U.S.C. 154(b) by 70 days.

(21) Appl. No.: 10/612,298

(22) Filed: Jul. 2, 2003

(65) Prior Publication Data

US 2004/0147716 A1 Jul. 29, 2004

Related U.S. Application Data

(60) Provisional application No. 60/394,176, filed on Jul. 3, 2002.

(51) Int. Cl.
*C40B 40/10* (2006.01)

(52) U.S. Cl. ........................... 506/18; 506/30; 533/333

(58) Field of Classification Search ....................... None
See application file for complete search history.

(56) References Cited

U.S. PATENT DOCUMENTS

| | | | | |
|---|---|---|---|---|
| 5,235,028 | A * | 8/1993 | Barany et al. | 528/335 |
| 5,753,628 | A | 5/1998 | Heavner et al. | |

FOREIGN PATENT DOCUMENTS

| | | | |
|---|---|---|---|
| EP | 0018072 | * | 10/1980 |
| JP | 07-188282 A | | 5/1995 |
| JP | 09173062 | * | 12/1995 |
| WO | WO 92/04371 | | 3/1992 |
| WO | WO 94/26296 | | 11/1994 |
| WO | WO 97/13522 | | 4/1997 |
| WO | WO 97/34923 | * | 9/1997 |
| WO | WO 00/62791 | | 10/2000 |
| WO | WO 01/39796 A2 | | 6/2001 |

OTHER PUBLICATIONS

Dooley et al. An all D-amino acid opioid peptide with central analgesic activity from a combinatorial library. 1994 Science 266:2019-2022.*
Lam et al. A new type of synthetic peptide library for identifying ligand-binding activity 1991 Nature 354:82-84.*
Satoh et al. Immobilization of saccharides and peptide on 96-will microtiter plates coated with methyl vinyl ether-maleic anhydride copolymer. 1998 Analytical Biochemistry 260:96-102.*
Janda, 1994 PNAS 91:10779-10785.*
R.B. Merrifield (1963 JACS 85:2149-2154).*
Dougherty et al (1996 Science 271:163-168).*
Komeda et al (1999 J. Molecular Catalysis B: Enzymatic 6:379-386).*
Sugihara et al (2002 J. Biochem. 131:247-254).*
Allured, V.S. et al., "Structure of exotoxin A of *Pseudomonas aeruginosa* at 3.0-Angstrom resolution," Proc. Natl. Acad. Sci (1986) 83:1320-1324.

Appella, D.H. et al., "Residue-based control of helix shape in beta-peptide oligomers," Nature (1997) 387(6631):381-384.
Choe, S. et al., "The crystal structure of diphtheria toxin," Nature (1992) 357:216-222.
Cook, C.L. et al., "Simple purification methods for an alpha-Galactose-specific antibody from chicken eggs," J. Biosci. & Bioeng. (2001) 91(3):305-310.
Craig, C. and Stitzel, R. eds., Modern Pharmacology, Little, Brown & Co., Boston (1986) 127-133.
Elliott, J.L. et al., "A quantitative study of the interactions of *Bacillus anthracis* edema factor and lethal factor with activated protective antigen," Biochemistry (2000) 39:6706-6713.
Endo, Y. et al., "The RNA N-glycosidase activity of ricin A-chain," J. Biol. Chem. (1988) 263:8735-8739.
Fryer, J.P. et al., "IgY antiporcine endothelial cell antibodies effectively block human antiporcine xenoantibody binding," Xenotransplantation (1999) 56:98-109.
Galili, U., "The alpha-gal epitope (Galalpha1-3Galbeta 1-4GlcNAc-R) in xenotransplantation," Biochimie (2001) 83:557-563.
Halloran, M.M. et al., "Ley/H: an endothelial-selective, cytokine-inducible, angiogenic mediator," J. Immunol. (2000) 164:4868-4877.
Kadlec, R.P. et al., "Biological Weapons Control. Prospects and Implications for the Future," J. Am. Med. Assoc. (1997) 278(5):351-356.
Kruszynski, M. et al., "Identification of TNF-alpha binding peptides from a D-amino acid hexapeptide library that specifically inhibit TNF-alpha binding to recombinant p55 receptor," Cytokine (1999) 11(1):37-44.
Laduca, J.R. et al., "Targeting tumor necrosis factor alpha. New drugs used to modulate inflammatory diseases," Dermatologic Clinics (2001) 19:617-635.
Lebl, M. et al., "One-bead-one-structure combinatorial libraries," Biopolymers (Peptide Science) (1995) 37:177-198.
Letterio, J.J., "Murine models define the role of TGF-beta as a master regulator of immune cell function," Cytokine & Growth Factor Reviews (2000) 11:81-87.
Lord, J.M. et al., "Ribosome inactivating proteins of plants," Semin. Cell Biol. (1991) 2:15-22.
Massague, J., "How cells read TGF-beta signals," Nature Review Mol. Cell Biol. (2000) 1:169-178.
Milne, J.C. et al., "Anthrax protective antigen forms oligomers during intoxication of mammalian cells," J. Biol. Chem. (1994) 269(32):20607-20612.

Moberg, L.J. et al., "Affinity chromatography purification of type A botulinum neurotoxin from crystalline toxic complex," Appl. Environ. Microbiol. (1987) 35(5):878-880.

(Continued)

*Primary Examiner*—Christopher Low
*Assistant Examiner*—Christopher M. Gross
(74) *Attorney, Agent, or Firm*—Barnes & Thornburg LLP; Alice O. Martin

(57) ABSTRACT

Disclosed are D-peptides and libraries of D-peptides comprising aromatic D-amino acids. Also disclosed are methods for identifying small D-peptides comprising aromatic D-amino acids that bind to proteins of interest.

2 Claims, No Drawings

OTHER PUBLICATIONS

Murphy, L.A. et al., "Five alpha-D-galactopyranosyl-binding isolectins from *Bandeiraea simplicifolia* seeds," J. Biol. Chem. (1977) 252:4739-4742.

Pinilla, C. et al., "All-D peptides recognized by an anti-carbohydrate antibody identified from a positional scanning library," J. Mol. Biol. (1998) 283:1013-1025.

Remington's Pharmaceutical Sciences, 18th Edition, Mack Pub. Co., Easton, PA (1990).

Shapiro, R.E. et al., "Identification of a ganglioside recognition domain of tetanus toxin using a novel ganglioside photoaffinity ligand," J. Biol. Chem. (1997) 272(48):30380-30386.

Speight, T, ed., Avery's Drug Treatment: Principles and Practice of Clinical Pharmacology and Therapeutics, 3rd ed. Williams and Wilkins, Baltimore (1987) 50-56.

Spilker, B., Guide to Clinical Studies and Developing Protocols, Raven Press Books, Ltd., New York (1984) 7-13, 54-60.

Spilker, B., Guide to Clinical Trials, Raven Press, Ltd., New York, (1991) 93-101.

Szekanecz, Z. et al., Chemokines and angiogenesis, Current Opinion in Rheumatology (2001) 13(3):202-208.

Tallarida, R. et al., Principles in General Pharmacology, Springer-Verlag, New York, (1988) 18-20.

Taylor, P.C., "Anti-tumor necrosis factor therapies," Current Opinion in Rheumatology (2001) 13(3):164-169.

Tse, C.K. et al., "Preparation and characterisation of homogeneous neurotoxin type A from *Clostridium botulinum*," Eur. J. Biochem. (1982) 122:493-500.

Wade, D. et al., "All-D amino acid-containing channel-forming antibiotic peptides," Proc. Natl. Acad. Sci, USA (1990) 87:4761-4765.

Kundu et al., "Combinatorial Approach to Lead Optimization of a Novel Hexapeptide with Antifungal Activity," *Bioorganic & Medicinal Chemistry Letters*, 10 (16): 1779-1781 (2000).

Supplementary Partial European Search Report issued in EP 03 76 3093 (2008).

\* cited by examiner

PEPTIDES COMPRISING AROMATIC D-AMINO ACIDS AND METHODS OF USE

CROSS-REFERENCE TO RELATED APPLICATIONS

This application claims the benefit of U.S. Provisional Patent Application Ser. No. 60/394,176, filed Jul. 3, 2002.

STATEMENT REGARDING FEDERALLY SPONSORED RESEARCH OR DEVELOPMENT

Not applicable.

BACKGROUND OF THE INVENTION

The biological activities of many proteins are modulated by binding of the proteins to other molecules. For example, lectins are a class of proteins whose activities are affected by binding to carbohydrates, including monosaccharides and oligosaccharides. Lectins are involved in many important functions, including, for example, active transport and chemotaxis in bacteria, establishing viral infections, mediating leukocyte-endothelial cell recognition, mediating attachment of bacteria or viruses to other cells, and recognizing normal or pathologic glycoproteins and polysaccharides. Because lectins are involved in important biological activities, they are attractive targets for drug therapy.

One approach to identifying a molecule with potential therapeutic value is to assess the ability of that molecule to bind to a protein having an important biological activity, because the activity of the protein may be altered by its binding to a molecule that does not normally serve as a substrate or ligand for the protein.

What is needed in the art are new compounds capable of binding to a protein of interest, and methods for identifying compounds having the ability to bind to a protein of interest.

BRIEF DESCRIPTION OF THE INVENTION

In one aspect, the present invention provides a D-peptide comprising a sequence of from three to seven D-amino acid residues, wherein at least two of the amino acid residues are independently selected from the group consisting of D-tryptophan, D-tyrosine and D-phenylalanine.

In another aspect, the present invention includes a D-peptide comprising a pentapeptide sequence selected from the group consisting of $Xaa_1YYFF$, $Xaa_1FYFF$, $Xaa_1YFFF$, $Xaa_1FFYF$, $Xaa_1YFFY$, $Xaa_1YFYF$, $Xaa_1FFFF$, $Xaa_1FYYF$, $FXaa_1FFF$, $YFXaa_1FF$, $Xaa_1FWXaa_2Y$, $Xaa_1FXaa_2WY$, $Xaa_1Xaa_2FFW$, $Xaa_1FFFY$, $FFFFXaa_1$, $YXaa_1YFF$, $YXaa_1FFY$, $Xaa_1FF$ $Xaa_2Xaa_3$, $Xaa_1WYFF$, $Xaa_1FXaa_2FF$, $Xaa_1YXaa_2FF$, $Xaa_1FFYXaa_2$, $Xaa_1FFXaa_2F$, $Xaa_1Xaa_2Xaa_3YY$, $Xaa_1Xaa_2Xaa_3FF$, $Xaa_1FYWF$, $Xaa_1Xaa_2FYY$, $Xaa_1YYFY$, $Xaa_1FYXaa_2Y$, $WXaa_1FFF$, $Xaa_1FFFXaa_2$, $Xaa_1YYYY$, $FXaa_1WFF$, $WXaa_1FWXaa_2$, $WFXaa_1FXaa_2$, $FWXaa_1FF$, $FXaa_1FFY$, $Xaa_1Xaa_2WXaa_3Y$, $FFWXaa_1Y$, $FXaa_1WXaa_2Xaa_3$, $YYXaa_1YY$, $FFFXaa_1F$, $YFYFXaa_1$, $YWXaa_1FF$, $WXaa_1YXaa_2F$, $WXaa_1YFXaa_2$, $WXaa_1FFXaa_2$, $FFFXaa_1W$, $FWFXaa_1Xaa_2$, $FYXaa_1YF$, $FWXaa_1Xaa_2Xaa_3$, $FXaa_1YYW$, $FXaa_1YYXaa_2$, $FWXaa_1WY$, $FFWYW$, $FXaa_1Xaa_2FXaa_3$, $FYWXaa_1Y$, $FYWXaa_1W$, $FXaa_1YFXaa_2$, $FWWYF$, $FYYYXaa_1$, and $FFXaa_1WW$, wherein $Xaa_1$, $Xaa_2$, and $Xaa_3$ are amino acids of the D- or L-configuration independently selected from the group consisting of D, E, K, R, H, N, Q, S, T, G, A, V, L, I, M, and P.

In another aspect, the present invention provides a library comprising a plurality of D-peptides, wherein each D-peptide comprises a sequence of from three to seven D-amino acid residues, wherein the sequences of at least 25% of the D-peptides comprise at least two amino acid residues independently selected from the group consisting of D-tryptophan, D-tyrosine, and D-phenylalanine.

In yet another aspect, the present invention provides a method for identifying a D-peptide having the ability to bind to a pre-selected protein comprising contacting a library of D-peptides according to the present invention with the protein, detecting binding of the protein to a D-peptide to yield a bound D-peptide, and identifying the bound D-peptide.

In yet another aspect, the present invention provides a method for making a D-peptide that binds to a pre-selected protein, comprising contacting a library of D-peptides according to the present invention with the protein, detecting binding of the protein to a D-peptide to yield a bound D-peptide, identifying the bound D-peptide, and synthesizing the D-peptide.

In an important aspect, the invention provides a method for reducing toxicity of a toxin in a mammal exposed to the toxin comprising delivering to the mammal a D-peptide of D-amino acids identified as binding to the toxin in an amount effective to reduce toxicity.

BRIEF DESCRIPTION OF THE DRAWINGS

Not applicable.

DETAILED DESCRIPTION OF THE INVENTION

In one aspect of the invention, the ability of proteins of interest to bind to D-peptides comprising D-aromatic acids was evaluated with the expectation that D-peptides having therapeutic utility would be identified. As used herein, a D-peptide is a peptide comprising amino acids of D-configuration. In addition to D-amino acids, D-peptides may further comprise L-amino acids. By proteins of interest, it is meant any protein having or suspected of having biological activity that may be altered by binding of a molecule to the protein. As discussed above, lectins mediate many important biological functions and therefore, are potentially useful targets in drug design. Other proteins of interest include, without limitation, protein toxins, such as those produced by various bacterial pathogens, and antibodies.

In order to test the ability of D-peptides to bind to pre-selected proteins of interest, libraries of pentapeptides enriched in aromatic D-amino acid residues were synthesized and then tested for the ability to bind to lectins, various protein toxins, various antibodies and other proteins. It is envisioned that libraries of short D-peptides ranging from three to seven amino acid residues in length could also be used to identify a D-peptide that binds to a protein of interest.

For libraries of D-peptides having from three to seven amino acid residues, a library enriched in D-peptides comprising aromatic D-amino acids is one in which about 25% or more of sequences in the library comprise two or more aromatic D-amino acid residues. Suitably, about 30% or more of the D-peptides comprise two or more aromatic D-amino acid residues. More suitably still, about 30% or more of the D-peptides comprise three or more aromatic D-amino acid residues. Still more suitably, 40% or even as many as 50% or more of the D-peptides comprise at least three or more aromatic D-amino acid residues.

As described in the Examples below, a pentapeptide library enriched in aromatic D-amino acids was constructed in a split synthesis method using four D-amino acids (alanine, phenylalanine, tyrosine, and tryptophan, or, using the one-letter codes for the amino acids, A, F, Y, and W, respectively) and glycine (G). Glycine is achiral and therefore, does not have D- or L-configurations. As used herein, the A, F, Y and W amino acids, or other amino acids, are of the D-configuration, unless otherwise specified. One wishing to create a library enriched in D-peptides comprising aromatic D-amino acids may do so using any suitable method. About 23% of the pentapeptides in the library made by the split synthesis method contain two aromatic D-amino acid residues, about 34% contain three aromatic D-amino acid residues, and about 25% contained four aromatic D-amino acid residues.

For D-peptide sequences in which an amino acid residue may be selected from any one of a number of amino acids, the residue may be designated "$Xaa_1$". In D-peptides having more than one amino acid residue selected from any one of a number of amino acids, such amino acid residues will be designated "$Xaa_1$", "$Xaa_2$", "$Xaa_3$", etc.

Suitably, the D-peptides in a library may be attached to a solid support. In the Examples below, a library of pentapeptides enriched in aromatic D-amino acids was synthesized on TentaGel beads, each of which has a polystyrene core and, attached to the core, a plurality of polyoxyethylene arms, each arm having a primary amine at its free end. D-peptides were synthesized by sequential conjugation of each amino acid residue added to the D-peptide, using conventional standard D-peptide synthesis chemistry. The D-peptides thus constructed have free amino termini. The split synthesis method yields beads each of which comprises multiple copies of a single D-peptide sequence. With five amino acids, the number of different pentapeptide sequences in the resulting library is $5^5$ or 3125.

Because the polyoxyethylene arms of the TentaGel beads are water soluble, the conformations of the D-peptides are determined primarily by thermodynamics and by their primary sequence. As one skilled in the art will appreciate, the D-peptide may be attached to any suitable support. For example, D-peptides comprising at least one lysine residue at the carboxy terminus were synthesized and covalently coupled to maleic anhydride-coated 96-well polystyrene plates for use in binding assays. The D-peptides thus coupled to the polystyrene plates have free amino termini.

Based on the results obtained in library screenings, summarized below in the Examples, the contribution of the aromatic amino acids F, Y, and W in the D-peptides of the present invention appears to be important for binding to proteins. Suitably, a D-peptide according to the present invention comprises a sequence of from three to seven D-amino acid residues in length, which sequence comprises at least two aromatic D-amino acid residues. More suitably, the sequence comprises at least three or four aromatic D-amino acid residues.

Although G and A were used as non-aromatic amino acids in the construction of the exemplified D-peptide libraries described below, the present invention is not restricted to D-peptides or D-peptide libraries comprising G and A residues. As an example, it is specifically envisioned that additional D-peptides or D-peptide libraries according to the present invention are suitably generated by replacing G and/or A with any one of the remaining D-amino acids (i.e., D, E, K, R, H, N, Q, C, S, T, V, L, I, M, and P). For example, by replacing G and A with D-serine (S) and D-leucine (L), an additional library of 3125 members each could be constructed. It is also envisioned that the G or A residues could be replaced with amino acids of the L-configuration producing libraries of mixed D- and L-configuration peptides.

It is reasonably expected that G or A could be replaced with "unusual" or "non-natural" amino acids of D- or L-configurations, e.g., D- or L-α-amino butyric acid, p-chloro-D-phenylalanine, p-chloro-L-phenylalanine, D-(2-naphthyl)alanine, or L-(2-naphthyl)alanine. Such unusual amino acids are commercially available as derivatives suitable for peptide syntheses. The library described in the Examples has D-peptides with the amino-terminus as a free amino group. It is envisioned that the free amino group may be derivatized, e.g., acetylated, and the resultant library of peptides tested for binding abilities to any protein of interest. It is further envisioned that a suitable library could be constructed in the same manner except by eliminating the free amino group at the amino termini of the D-peptides. This could be accomplished by adding at the last step of the construction of the library the compounds acetic acid, propionic acid, 3-phenyl-propionic acid, 3-(4-hydroxy-phenyl)-propionic acid or 3-indole-propionic acid.

It is further envisioned that a D-peptide sequence identified as binding to a protein of interest could be used to design additional libraries by replacing the non-aromatic residues with other non-aromatic residues. For example, if a D-peptide having an A residue at a particular position is identified as binding to a protein, other sublibraries could be readily constructed with permutations at the A position. A sublibrary comprising additional D-peptides could be constructed by replacing A with one of the amino acids not used in the construction of the original library. For a D-peptide sequence having G or A at two or more positions, one could replace the residues at 2 positions where a G or A residue is found with different amino acids to create a new sublibrary with 196 members. Sublibraries thus created could be screened to identify members with different binding specificity or affinity for the protein of interest than the originally identified D-peptide.

An aromatic compound library could also be constructed using building blocks that are not amino acids. For example, α-hydroxy- or β-hydroxy-carboxylic acids with aromatic constituents on the α- or β-carbons could be used and the individual carboxylic acids coupled to each other via formation of ester bonds. The library could be built using the appropriate carboxylic analogues of G, A, F, Y and W (e.g., glycolic acid, lactic acid, phenyl-lactic acid, 3-(4-hydroxyphenyl)-lactic acid or 3-indole-lactic acid) using carbodiimide catalyzed couplings, and screened for binding to a protein of interest as described in the Examples below.

A suitable library could be built using β-amino acids composed of the appropriate analogues of the amino acids G, A, F, Y and W on TentaGel beads in the same manner as done for the D-configuration α-amino acids. Synthesis of D-peptides using β-amino acids analogues was described in Applella et al., (*Nature*, 387, 381-384, 1997), which is incorporated by reference herein.

A pre-selected protein used in screening the D-peptide libraries of the present invention may be any protein of interest, including lectins, protein toxins, or antibodies, for example. In the Examples below, the jack bean lectin (ConA), the garden pea lectin (PSA), and the lectin designated GSI-B4, as well as two anti-carbohydrate antibodies, were used to screen the D-peptide library for the ability to bind proteins. Competitive binding assays described below in the Examples suggest that D-peptides may bind to carbohydrate binding sites. However, it should be understood that the present invention is not limited only to those D-peptides that bind to carbohydrate binding sites.

In other Examples, proteins toxins, including botulinum toxins, ricin toxins, cholera toxin, and a component of the anthrax toxin, were screened for the ability to bind to D-peptides. It is of particular interest to identify molecules that can interact with toxins such as these because of the potential for biological warfare using toxins. For each toxin tested, D-peptides having the ability to bind to the proteins were identified.

*Clostridium botulinum* produces seven types of botulinum neurotoxins designated BoNT/A-BoNT/G. The toxins inhibit release of acetylcholine from the pre-synaptic neurons into the neuronal synapse, which may ultimately cause paralysis. Binding of the toxin to cells is required for toxicity. Blocking the binding of the botulinum toxins to the target cells, or blocking the protease activities of the neurotoxins, would prevent or reduce the pathogenic effects of the toxins.

In the Examples below, D-peptides that bind to BoNT/A, BoNT/B or BoNT/E were identified. A mixture of three D-peptides having the ability to bind BoNT/A were administered to mice injected with the BoNT/A toxin. Preliminary data using live mice suggest that the D-peptides reduce toxicity of the BoNT/A toxin in mammals.

The botulinum toxin binding domain resembles other toxins, including the tetanus neurotoxin (TeNT) (Shapiro et al., *J. Biol. Chem.*, 272, 30380-30386, 1997), diptheria toxin (Choe et al., *Nature,* 357, 216-222, 1992) and *Pseudomonas aeriginosa* exotoxin A (Allerud et al., *Proc. Natl. Acad. Sci.,* 83, 1320-1324, 1986). It is therefore expected that D-peptides having the ability to bind to TeNT, diptheria toxin, and exotoxin A will be identified using libraries according to the present invention, and that such D-peptides may reduce toxicity of the toxins in a mammal.

Ricin is a plant cytotoxin composed of a cell surface binding domain (B) and an enzymatically active A domain with N-glycosidase activity (Lord et al., *Semin. Cell Biol.,* 2, 15-22, 1991). The B domain binds to galactose residues of a cell surface and the A domain cleaves a single adenine from a conserved sequence of rRNA thus inactivating the ribosome and resulting in cell death. (Endo and Tsurugi, *J. Biol. Chem.,* 263, 8735-8739, 1988). The identification of a D-peptide having the ability to bind to ricin may reduce binding of the toxin to cells or reduce its activity, thereby reducing toxicity.

The cholera toxin has one A subunit and five B subunits, and is similar in overall structure to the *E. coli* enterotoxin, the *Shigella dysenteriae* toxin and the *Bordetella pertussis* toxin. The cholera toxin binds to cell surface ganglioside $GM_1$ on the luminal surface of intestinal epithelial cells, where the A subunit is internalized and modifies guanine nucleotide-binding proteins involved in regulation of adenylate cyclase. Blocking the binding of the B subunit to the target cells will block A subunit internalization and reduce toxicity associated with the toxin.

The anthrax toxin has three components: the protective antigen (PA), lethal factor (LF) and edema factor (EF). The PA binds to the host cell surface receptor, is cleaved by a furin-like protease and the carboxy-terminal fragment heptamerizes and binds LF or EF (Milne et al., *J. Biol. Chem.,* 269, 20607-20612, 1994; Elliott et al., *Biochemistry,* 39, 6706-6713, 2000). The EF and LF are translocated to the cytosol of the host cell, where EF activates an adenylate cyclase activity and LF, a protease, cleaves members of the mitogen-activated protein kinase family. Binding of a D-peptide to a component of the anthrax toxin could reduce toxicity.

In other Examples, antibodies were screened for the ability to bind to D-peptides in the D-peptide library. One antibody tested was an antibody which binds to a carbohydrate epitope composed of the H and Ley carbohydrate sequences, which binds to an antigen of endothelial cells and inhibits activities associated with an angiogenic response (Szekanecz and Koch, *Current Opinion_in Rheumatology,* 13:202-208, 2001). The D-peptide identified as binding to the antibody may be used to study angiogenesis or to act as an agonist or antagonist of angiogenesis. A human antibody to an α-Gal epitope involved in the primate rejection response to transplanted porcine organs (Galili, *Biochimie* 83:557-563, 2001) was screened to identify D-peptides that bind to the antibody. Those D-peptides may be useful in blocking rejection mechanisms mediated by the human anti-α-Gal antibodies.

In other Examples, TNFα and TGFβ1 were screened for their ability to bind D-peptides, and several D-peptide sequences were identified. TNFα and TGFβ1 are proteins involved in many cell signaling pathways (LaCuca and Gaspari, *Dermatologic Clinics* 19:617-635, 2001; Taylor, *Current Opinion in Rheumatology* 13:164-169, 2001; Massague, *Nature Review Molecular Cell Biology* 1:169-178, 2000; Letterio, Cytokine & *Growth Factor Reviews* 11:81-87, 2000). The D-peptides identified could be used to study signaling pathways or as possible therapeutic agents in pathologies in which TNFα and TGFβ1 are involved as mediators.

After a D-peptide has been identified as binding to a pre-selected protein according to the method of the present invention, one of ordinary skill in the art can readily synthesize the D-peptide in sufficient quantity for further evaluation or for use as a therapeutic, which can be used to alter the activity of the pre-selected protein or, in the case of a protein toxin, reduce the toxicity of the toxin.

For those D-peptides of the present invention intended for administration to a mammal, (e.g., a mammal exposed to a toxin), the D-peptides are suitably constructed or modified so as to enhance solubility. In the Examples below, D-peptides administered to mice were designed and synthesized to include three D-lysine residues at the C-terminal ends of the D-peptides to enhance solubility. It is envisioned that from one to four D-lysine residues at the C-terminus would enhance solubility. It is further envisioned that any amino acid residue tending to promote solubility could be included at the C-terminus, including R, D and/or E amino acids. It is yet further envisioned that the D-peptides could be derivatized at the C-terminus with substituents other than amino acids to promote solubility. Such substituents may include a polyoxyethylene polymer or a compound containing multiple hydroxyl groups, such as monosaccharide or polysaccharide. It is also envisioned that one or more of the D-peptides may be chemically coupled to a water soluble compound such as a polysaccharide or protein to promote solubility in water-based solvents or physiologic fluids. It is envisioned that the D-peptides could be physically incorporated into or chemically coupled to structures such as liposomes in order to promote solubility in water-based physiologic fluids. It is further envisioned that more than one D-peptide could be coupled to a carrier molecule so as to multimerize the resulting conjugated compound for administration to a mammal with the potential effect of achieving a functional affinity (avidity) of the D-peptide multimer. It is yet further envisioned that more than one D-peptide identified as binding to a protein of interest may be coupled to a carrier compound to potentially achieve functional affinity effects. Additionally, it is envisioned that one or more of the D-peptides may be conjugated to another peptide, protein or carbohydrate sequence (for example, the sialyl-lactose carbohydrate sequence known to have a binding site on the botulinum neurotoxin) in order to enhance binding of such conjugates to a protein of interest.

The polypeptide sequence according to the present invention can be administered in any acceptable manner including orally, parenterally, nasally, by implant, and the like. Oral administration includes administration in tablets, suspension, implants, solutions, emulsions, capsules, powders, syrups, water composition, and the like. Nasal administration includes administering the composition of the present invention in sprays, solutions, and the like.

The therapeutic agents useful in the method of the invention can be administered parenterally by injection or by gradual perfusion over time. Administration may be intravenously, intra-peritoneally, intramuscularly, subcutaneously, intra-cavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, intravenous vehicles including fluid and nutrient replenishers, electrolyte replenishers (such as those based on Ringer's dextrose), and the like. Preservatives and other additives may also be present, such as antimicrobials, anti-oxidants, chelating agents or inert gases and the like.

The actual dosage of a polypeptide sequence of the invention, formulation, or composition will depend on many factors, including the size and health of an individual. However, the appropriate dosage may be determined by one of ordinary skill in the art. The following teachings, which are incorporated by reference, provide guidance: Spilker B., *Guide to Clinical Studies and Developing Protocols*, Raven Press Books, Ltd., New York, 1984, pp. 7-13, 54-60; Spilker B., *Guide to Clinical Trials*, Raven Press, Ltd., New York, 1991, pp. 93-101; Craig C., and R. Stitzel, eds., *Modern Pharmacology*, d. ed., Little, Brown and Co., Boston, 1986, pp. 127-33; T. Sleight, ed., *Avery's Drug Treatment: Principles and Practice of Clinical Pharmacology and Therapeutics*, 3d ed., Williams and Wilkins, Baltimore, 1987, pp. 50-56; R. Tallarida, R. Raffa and P. McGonigle, *Principles in General Pharmacology*, Springer-Verlag, New York, 1988, pp. 18-20. A polypeptide sequence of the invention may be conveniently administered in unit dosage form, and may be prepared by any of the methods well known in the pharmaceutical art, for example, as described in *Remington's Pharmaceutical Sciences* (Mack Pub. Co., Easton, Pa., 1990).

Physiologically acceptable and pharmaceutically acceptable excipients and carriers are well known to those of skill in the art. By "physiologically or pharmaceutically acceptable carrier" as used herein it is meant any substantially non-toxic carrier for administration in which a polypeptide sequence of the invention will remain stable and bioavailable when used. For example, the polypeptide sequence of the invention can be dissolved in a liquid, or dispersed or emulsified in a medium in a conventional manner to form a liquid preparation or mixed with a semi-solid or solid carrier to form a paste, ointment, cream, lotion or the like.

Suitable carriers include water, petroleum jelly (VASELINE®), petrolatum, mineral oil, vegetable oil, animal oil, organic and inorganic waxes, such as microcrystalline, paraffin or ozocente wax, natural polymers, such as xanthanes, gelatin, cellulose, or gum arabic, synthetic polymers, alcohols, polyols, water and the like. A water miscible carrier composition that is substantially miscible in water can be used. Such water miscible carrier compositions can include those made with one or more ingredients set forth above but can also include sustained or delayed release carrier, including water containing, water dispersible or water soluble compositions, such as liposomes, microsponges, microspheres or microcapsules, aqueous base ointments, water-in-oil or oil-in-water emulsions, or gels.

The carrier can comprise a sustained release or delayed release carrier. The carrier may be any material capable of sustained or delayed release of the polypeptide sequence. The carrier is capable of releasing the polypeptide sequence when exposed to the environment of the area of intended delivery by diffusing or by release dependent on the degree of loading of the sequence to the carrier in order to obtain release of the polypeptide of the invention. Nonlimiting examples of such carriers include liposomes, microsponges, microspheres, matrices, or microcapsules of natural and synthetic polymers and the like. Examples of suitable carriers for sustained or delayed release in a moist environment include gelatin, gum arabic, xanthane polymers; by degree of loading include lignin polymers and the like; by oily, fatty or waxy environment include thermoplastic or flexible thermoset resin or elastomer including thermoplastic resins such as polyvinyl halides, polyvinyl esters, polyvinylidene halides and halogenated polyolefins, elastomers such as brasiliensis, polydienes, and halogenated natural and synthetic rubbers, and flexible thermoset resins such as polyurethanes, epoxy resins and the like. The sustained or delayed release carrier can be a liposome, microsponge, microsphere or gel. A pH balanced buffered aqueous solution for injection can be used. As one of skill in the art will appreciate, the preferred carrier will vary with the mode of administration. The compositions for administration usually contain from about 0.0001% to about 90% by weight of the polypeptide sequence compared to the total weight of the composition.

The D-peptide libraries may be useful in identifying D-peptides that may be used in affinity chromatographic purification of the pre-selected protein of interest. The D-peptides can readily be covalently coupled, using well-known chemistries, to any one of a number of suitable matrices used in chromatographic separations. The D-peptide matrices could be used to bind to the pre-selected protein from mixtures followed by elution and recovery of the protein.

The following nonlimiting examples are intended to be purely illustrative.

EXAMPLES

Peptide Library Design and Synthesis

A D-peptide library was synthesized by Peptides International, Louisville, Ky. using a TentaGel S resin, $NH_2$ ("TentaGel beads"). With the exception of glycine, which is an achiral molecule, all of the amino acid residues in the D-peptides are of the D configuration. The TentaGel beads have a polystyrene core with polyoxyethylene arms attached to the core; each arm has a primary amine functional group at its terminus. The resin contains $8.87 \times 10^5$ beads/gram, an average bead diameter of 130 microns, 0.2-0.3 meq/gram capacity and 280-330 pmole of primary amine groups/bead capacity. The amino acids were conjugated to the resin and deprotected using standard D-peptide synthetic chemistries.

Amino acids will be designated with the one-letter code. All amino acids are of the D-configuration unless otherwise noted. Glycine was attached to the resin to achieve about a 30% substitution of the available primary amine groups at the ends of the polyoxyethylene chains of the Tent-Gel beads. The amine groups to which glycine was not added were blocked by acetylation using acetic anhydride. A 30% substitution yields an average spacing of about 100 to 200 angstroms between D-peptides on the bead surface. The spacing was chosen to optimize binding of a single protein to a single D-peptide sequence, and to reduce the likelihood that steric hindrance will prevent a protein molecule from binding to a D-peptide or that a protein molecule will bind to more than one D-peptide.

Following blocking of the unreacted primary amine groups, the D-peptide library was built by the split synthesis method (Lebl et al., *Biopolymers* (*Peptide Science*), 37, 177-198 (1995). The resin mixture was divided equally into five portions and one of G, A, F, Y or W was added by covalent coupling to one of the five portions of the G-substituted resin. The beads were then combined, again equally divided into five portions, and each portion was used in reactions in which one of G, A, F, Y or W was added in the separate reaction mixtures. The procedure was repeated for the five cycles to yield a library of pentapeptide sequences attached to the G residues of the resin. Each bead contained multiple copies of a single D-peptide sequence. Because five amino acids were used at each of five amino acid adding steps, the resulting bead library contains 3125 pentapeptide sequences. Following the final amino acid addition, the resin batches were kept separate, which resulted in five sublibraries of 625 different sequences, designated G, A, F, Y, or W, according to the last amino acid added.

Screening for Protein Binding to D-Peptides and Results of Binding Assays to the D-Peptide Substituted Beads (Peptide-Beads)

In general, except as otherwise noted, proteins were screened for binding to the D-peptide beads as follows.

An aliquot from each sublibrary, each aliquot containing approximately 1000 beads, was added to a well of a 24-well polystyrene multi-well plate. From 1.5 to 2 ml Superblock (Pierce Chemical Company, Rockford, Ill.) reagent, 0.1% gelatin (fish skin gelatin, Sigma Chemical Company, St. Louis, Mo.), or 1% (w/v) bovine serum albumin (BSA, Sigma Chemical Company) in phosphate buffered saline (PBS), pH 7.4, was added to each well, and the plates were incubated for one to two hours at room temperature (RT), with periodic or continuous mixing by gentle rocking. The protein to be tested for binding was diluted in Superblock or 0.1% gelatin-PBS to give a final concentration of about $10^{-6}$ to $10^{-8}$ M. The diluted protein solution was incubated with the D-peptide-beads for one to two hours at RT. Following the incubation, the protein solution was removed and the beads washed three times with PBS. In the second wash, PBS was left on the beads for about 30 minutes to allow dissociation of weakly binding protein.

After washing with PBS, an agent for detecting bound protein was added. In some cases, the test protein was labeled with alkaline phosphatase (AP) and no secondary detection agent was required. In other cases, the test protein was labeled with biotin using the biotinylating reagent NHS-LC-biotin (Pierce Chemical Company) according to the supplier's instructions. Biotin-labeled protein was detected using AP conjugated to neutravidin (Pierce Chemical Company). Another means of detecting bound biotinylated proteins used AP-conjugated anti-biotin antibody reagent, which detects bound biotinylated protein on the beads. In other instances, the detection reagent was an AP-labeled antibody to the protein. The detection agents were generally incubated with the beads for 30 minutes, after which the beads were washed three times with a Tris-buffered saline solution (pH 7.5), with the second wash being left in contact with the beads for 30 minutes. One-step NBT/BCIP (nitro-blue tetrazolium chloride/5-bromo-4-chloro-3'-indolylphosphate p-toluidine salt) (Pierce Chemical Co.) was then added and the beads observed under a low power microscope until some of the beads had turned a dark purple to purple-black (dark purple-black) color. In the presence of AP enzyme, the phosphoryl group from BCIP is hydrolyzed and the BCI product reacts with NBT which then forms NBT-formazan. The NBT-formazan forms a purple-black precipitate on the beads to which the AP is attached. The beads were then washed with PBS twice, followed by a 1% acetic acid wash, and finally, water. The Fast Red TR/AS-MX substrate kit (Pierce Chemical Co.), which yields a bright red precipitate on beads positive for AP, was used in one experiment. The latter dye-precipitate can be removed by washing the beads with ethanol.

Dark purple-black beads, or bright red beads (when the Fast Red substrate was used), were removed using a small bore pipette and subjected to amino acid sequence analysis performed at the Core Laboratories of Louisiana State University Health Sciences Center. The sequences obtained were essentially unequivocal. Because the five sublibraries were kept separate, the first residue at the amino-terminus was known. For all D-peptides in the library, the sixth amino acid is G because G was coupled to the TentaGel beads. For purposes of reporting the D-peptide sequences, the sixth residue (G) is not reported.

Binding of Lectins PSA (*Pisum sativum*, Garden Pea Lectin) and ConA (*Canavalia ensiformis*, Jack Bean Lectin) to D-Peptide-Beads The lectins as conjugated with AP (AP-PSA and AP-ConA) were purchased from EY Laboratories (San Mateo, Calif.). The lectins were incubated with the F and Y sublibraries by the procedure outlined above. The number of purple-black beads and the number of total beads were counted in each incubation well, and the percent positive beads was calculated. The approximate number of positive sequences was calculated based on 625 different D-peptide sequences each in the F- and Y-sublibraries.

TABLE 1

Binding of AP-ConA and AP-PSA Lectins to F and Y Sublibrary D-peptide Beads

|  | Percent positive | Number of positive beads/ 625 possible sequences |
|---|---|---|
| AP-ConA |  |  |
| F Sublibrary | 2.1 | 13 |
| Y Sublibrary | 1.3 | 8 |
| AP-PSA |  |  |
| F Sublibrary | 2.6 | 16 |
| Y Sublibrary | 1.6 | 10 |

The relatively low percentage of positives obtained suggests that the binding between the D-peptides of the F and Y sublibraries and the lectins was selective. If proteins bound to the beads only due to the hydrophobicity of the D-peptide sequences, one would have expected to obtain a high percentage of positives. On the other hand, if the proteins had failed to bind to any of the D-peptide sequences, one might conclude that D-peptides do not fit into the lectin binding sites or to other surface areas of the lectin proteins. Instead, the results showed that the frequency of binding of the lectins was selective for a small percentage of the D-peptide sequences. Control experiments showed that the AP enzyme was not responsible for binding to D-peptide sequences.

The amount of protein binding to a bead was calculated to be about 5 pmoles protein/bead, based on the following assumptions: (1) AP-PSA and AP-ConA were added in a one ml volume to the beads and at a concentration of $10^{-7}$ M; (2) the Kd for the D-peptide sequence and lectin complexes is assumed to be about $10^{-7}$ M; (3) one-half of the total AP-ConA or AP-PSA protein is bound at equilibrium; and (4) an average of about 10 beads out of a 1000 are positive.

Cross-Reactivity of D-Peptide-Beads for AP-ConA and AP-PSA

To evaluate the ability of particular D-peptides to bind to both AP-ConA and AP-PSA, the F- and Y-sublibraries were incubated with either AP-ConA or AP-PSA. Positive beads were detected using the Fast Red TR/AS-MX substrate. The positive beads were removed, and the dye washed from the beads using ethanol. The original AP-ConA positive beads were then incubated with AP-PSA, and the original AP-PSA positive beads were incubated with AP-ConA. Positive beads were then detected using the NBT/BCIP dye reagent and the number of positive beads (purple-black color) was determined. Of 11 beads tested from the Y-sublibrary that were initially positive for AP-ConA binding, 3 (27%) were positive for AP-PSA binding. One of 9 (11%) Y-sublibrary initially positive for binding of AP-PSA was positive for AP-ConA binding. Of 26 beads from the F-sublibrary originally positive for AP-PSA, 8 (31%) were positive for binding of AP-ConA. Neither of the two beads from the F-sublibrary that were positive for AP-ConA binding bound to AP-PSA. Of the total beads tested (48), 12 (25%) were cross-reactive for both lectins. Thus, for lectins that share binding specificities for similar carbohydrate structures, certain D-peptide sequences may exhibit cross-reactive binding activities. ConA and PSA lectins have specificity for structures containing mannose in an α-anomeric glycosidic linkage at the non-reducing termini of oligosaccharides. It is therefore not surprising that certain of the D-peptides to which the lectins bind are the same, and that certain D-peptides may bind to more than one lectin.

Competitive Binding for Lectins Between D-Peptide Beads and the Carbohydrate Ligand To test whether the lectins bind to D-peptide sequences through their carbohydrate binding sites, the D-peptide-beads of the F- and Y-sublibraries were incubated with AP-ConA in the presence and absence of 10 mM concentration of α-methyl-mannoside. The beads were then incubated with NBT/BCIP reagent. In the absence of aα-methyl-mannoside, 7.9% and 5.7% of D-peptides of the F- and Y-sublibraries, respectively, bound ConA. When incubated with the D-peptides in the presence of α-methyl-mannoside, ConA bound to 4.0% and 1.2% of the D-peptides in the F- and Y-sublibraries, respectively. The results suggest that approximately half of the positive D-peptide sequences in the F-sublibrary and a fifth of the positive D-peptides in the Y sublibrary D-peptide bind to the same binding site as that to which α-methyl-mannoside binds.

In an additional experiment, the F- and Y-sublibrary beads were first incubated with AP-ConA in the presence of α-methyl-mannoside yielding 2.1% of the Phe and 1.1% of the Tyr beads as positive. Those beads were removed from the incubation wells and the beads further incubated with AP-ConA without added α-methyl-mannoside. After the substrate NBT/BCIP was added, 3.6% of the Phe and 5.6% of the Tyr sublibraries turned dark purple-black again illustrating that a portion of the D-peptide sequences in each sublibrary were binding to the carbohydrate binding site of the ConA lectin.

Binding of Chicken Antibody and a Lectin to D-Peptides

An affinity-purified chicken antibody developed against an antigen comprising an (Gal epitope (Cook et al., *J Biosci.*& *Bioeng.*, 91, 305-310, 2001) and a biotinylated lectin that binds to the same epitope, GS 1, B4 isoform (Murphy and Goldstein, *J. Biol. Chem.*, 252, 4739-4742, 1977) were tested for binding to the A- and G-sublibraries. Binding of chicken antibody to beads was detected using an AP-labeled secondary antibody to chicken IgY. Binding of the lectin to beads was detected using AP-neutravidin. The chicken antibody and lectin were incubated with the beads at a concentration of 50 μg/ml, about 0.3 μM and 0.44 μM, respectively. The percentage of D-peptides binding to the antibody or lectin was determined as described above.

TABLE 2

Frequencies of Binding of Chicken Anti-αGal Antibody and the Lectin GS1-B4 to the G- or A-Sublibraries of D-peptide Beads

|  | Percent positive | Number of positive beads 625 possible sequences |
|---|---|---|
| Chicken anti-αGal |  |  |
| A sublibrary | 0.07 | 1 |
| G sublibrary | 0.6 | 4 |
| GS1-B4 lectin |  |  |
| A sublibrary | 2.9 | 18 |
| G sublibrary | 3.8 | 24 |

These results show that an antibody to a carbohydrate epitope, as well as a lectin with a binding site to the same carbohydrate epitope, exhibit specificity in binding to the D-peptide sequences. Furthermore, the results show that a lectin with reactivity to a carbohydrate epitope different from that of ConA and PSA, exhibits binding to D-peptide sequences.

Binding Specificities of Two Additional Antibodies Reactive with Carbohydrate Epitopes to D-Peptide Sequences A biotinylated mouse IgM monoclonal antibody to a Ley/H carbohydrate epitope (Holloran et al., *J. Immunol.*, 164, 4868-4877, 2000) or affinity-purified human anti-αGal antibody, (Fryer et al., *Xenotransplantation*, 56:98-109, 1999) were incubated with D-peptides from the A-, G-, F-, Y-, and W-sublibraries. Binding to the D-peptides was detected using AP-labeled anti-mouse IgM reagent (Sigma) or AP-labeled anti-human Ig reagent (Sigma Chemical Co.). The percentage of D-peptides binding to the antibodies are shown in Table 3, below.

TABLE 3

Frequencies of Binding of Two Anti-carbohydrate Antibodies to the D-peptide Beads

| Sublibrary | Percent positive | Number of positive beads/ 625 possible sequences |
|---|---|---|
| Mouse anti-Ley/H |  |  |
| A | 0 | 0 |
| G | 0.4 | 3 |
| F | 0 | 0 |
| Y | 0.5 | 3 |
| W | 0.5 | 3 |

TABLE 3-continued

Frequencies of Binding of Two Anti-carbohydrate Antibodies to the D-peptide Beads

| Sublibrary | Percent positive | Number of positive beads/ 625 possible sequences |
|---|---|---|
| AP-labeled anti-mouse IgM reagent | | |
| A | 0 | 0 |
| G | 0.5 | 3 |
| F | 0 | 0 |
| Y | 0 | 0 |
| W | 0 | 0 |
| Human anti-αGal | | |
| A | 0.1 | 1 |
| G | 0.2 | 1 |
| F | 0 | 0 |
| Y | 0 | 0 |
| W | 0 | 0 |
| AP-labeled anti- human IgG reagent | | |
| A | 0 | 0 |
| G | 0 | 0 |
| F | 0 | 0 |
| Y | 0 | 0 |
| W | 0.1 | 1 |

The results show that two additional anti-carbohydrate antibodies exhibit selective binding to the D-peptide beads. The mouse anti-Ley/H antibody was reactive with D-peptide sequences of the Y and W sublibraries. The antibody also bound D-peptides from the G sublibrary, but binding did not exceed background (i.e., AP-labeled anti-mouse IgM reagent bound to the same number of sequences in the presence and absence of anti-Ley/H antibody). The human anti-αGal antibody appeared to bind to D-peptide sequences of the A and G sublibraries; the AP-labeled anti-human Ig reagent only bound to one sequence of the W sublibrary. Thus, the D-peptide sequences appear to be specific for another form of anti-αGal antibody (human) compared to the chicken anti-αGal antibody in the previous example. It was not determined whether the human and chicken anti-αGal antibodies bound to the same D-peptide sequences on the TentaGel beads.

Preparation of Toxins

In the Examples that follow, several toxins were screened for the ability to bind to D-peptide sequences in the D-peptide bead library. The toxins include the neurotoxin component of the botulinum toxins, the cell binding B subunit of the cholera toxin, the protective antigen portion of the anthrax toxin, and the cell binding component of the ricin toxin. These toxins are particularly important because of their potential for use in biological warfare agents (*J. Am. Med. Assoc.*, vol. 278, no. 5, Aug. 6, 1997).

The neurotoxin components of the A, B and E serotypes of the botulinum toxins, and the botulinum type B complex form (designated BoNT/A, BoNT/B, BoNT/E and BotBcomp, respectively) were purified by methods described by Tse et al. (*Eur. J. Biochem,* 122, 493-500, 1982) and Moberg and Sugiyama (*Appl. Environ. Microbiol.,* 35, 878-880, 1987). The two forms of the ricin toxin (RCA60 and RCA120) were purchased from Sigma Chemical Co. (St. Louis, Mo.). The cholera toxin B subunit was purchased from List Biological Laboratories, Campbell, Calif. The protective antigen (PA) component of the anthrax toxin was kindly supplied by the United States Army Medical Research Institute of Infectious Diseases.

Frequency of Binding of BoNT/A and BoNT/B to D-Peptide Beads

Biotinylated BoNT/A and BoNT/B neurotoxins were incubated with the five sublibraries of D-peptide beads, and binding detected using the AP-neutravidin reagent, as described above. The frequencies of strong positive (purple-black) beads were determined.

TABLE 4

Frequencies of Binding of BoNT/A and BoNT/B Neurotoxins to the D-peptide Beads

| Sublibrary | Conc[#], (ug/ml, nM) | Percent positive | Number of positive beads/ 625 possible sequences |
|---|---|---|---|
| BoNT/A | | | |
| G | 100, 667 | 0.2 | 1 |
| G | 10, 67* | 0.3 | 2 |
| G | 10, 67* | 0 | |
| G | 10, 67* | 0.2 | 1 |
| G | 1, 6.7 | 0 | |
| A | 100, 667 | 0.2 | 1 |
| A | 10, 67* | 0 | |
| A | 10, 67* | 0 | |
| A | 10, 67* | 0 | |
| A | 1, 6.7 | 0 | |
| F[+] | 100, 667 | 0.1 | 1 |
| Y[+] | 100, 667 | 0 | |
| W[+] | 100, 667 | 0 | |
| BoNT/B | | | |
| G | 10, 67 | 2.3 | 14 |
| G | 5, 33 | 0.5 | 3 |
| G | 1, 6.7 | 1.0 | 6 |
| G | 0.1, 0.67 | 0 | |
| A | 10, 67 | 1.6 | 10 |
| A | 5, 33 | 0 | |
| A | 1, 6.7 | 0.1 | 1 |
| A | 0.1, 0.67 | 0 | |
| F | 10, 67 | 0.7 | 4 |
| F | 5, 33 | 0 | |
| F | 1, 6.7 | 0.1 | 1 |
| F | 0.1, 0.67 | 0 | |
| Y | 10, 67 | 0.6 | 4 |
| Y | 5, 33 | 0 | |
| Y | 1, 6.7 | 0.3 | 2 |
| Y | 0.1, 0.67 | 0 | |
| W | 10, 67 | 1.0 | 6 |
| W | 5, 33 | 0 | |
| W | 1, 6.7 | 0 | |

[#]Concentration of toxin in the incubation with the D-peptide beads.
*Assay for binding to the beads was repeated 3 times at the 10 ug/ml concentration.
[+]There was no binding of the BoNT/A toxin to the D-peptide beads at the 10 and 1 ug/ml concentrations.

The results indicate that, as expected, the frequency of positives diminishes as the concentration of the toxin incubated with the beads is decreased below the sensitivity of detection. For example, binding of BoNT/A to D-peptides in the G sublibrary was detectable at BoNT/A concentrations of 667 nM and 67 nM, whereas binding of BoNT/A to D-peptides in the A and F sublibraries was detectable only at a BoNT/A concentration of 667 nM. The selectivity of the D-peptides for the toxins is suggested by the low frequencies of binding. The higher binding frequencies observed for the BoNT/B toxin may be due to differential biotinylation of BoNT/B and BoNT/A, to an effect on the BoNT/A activity due to biotinylation, or due to the greater activity of the particular purified preparations used in the screening assays.

Frequencies of Binding of Ricin Toxin (RCA60), Anthrax Protective Antigen (PA) and Cholera Toxin B Subunit (CT) to D-Peptide Beads The RCA60 form of the ricin toxin, the PA protein and the B subunit of the cholera toxin were biotinylated, incubated with the D-peptide library beads, and binding detected using the AP-neutravidin reagent. Numbers of positive beads were counted and the frequencies calculated.

TABLE 5

Frequencies of Ricin (RCA60), Protective Antigen (PA) and Cholera Toxin (CT) Binding to D-peptide Beads

| Sub-library | Conc#, (ug/ml, nM) | Percent positive | Number of positive beads/ 625 possible sequences |
|---|---|---|---|
| RCA60 | | | |
| G | 5, 83 | 0.5 | 3 |
| A | " | 0.8 | 5 |
| F | " | 2.8 | 18 |
| Y | " | 1.4 | 9 |
| W | " | 2.3 | 14 |
| PA | | | |
| G | 23, 40 | 0.5 | 3 |
| A | " | 0.4 | 3 |
| F | " | 0.4 | 3 |
| Y | " | 0.2 | 1 |
| W | " | 0.2 | 1 |
| CT | | | |
| G | | 0.3 | 2 |
| A | | 0 | |
| F | | 0.2 | 1 |
| Y | | 0 | |
| W | | 0.4 | 3 |

Concentration of the protein in the incubation with the D-peptides.

The results showed selective binding of the D-peptide sequences to each toxin component tested.

Additional binding studies were performed with the BoNT/E toxin, with the RCA120 form of ricin, and with the botulinum B complex toxins (BotB complex).

Sequences of Positive Beads from the Binding Assays with the Various Proteins

Positive beads identified in binding assays were selected at random and the amino acid sequences determined for the individual beads. The sequences are shown in Table 6.

TABLE 6

Sequences of D-peptides binding to tested lectins or toxins.

| Lectin or Toxin | Sequences |
|---|---|
| ConA | GYYFF; GFYFF |
| BoNT/A | GYFFF; GFFYF; GFFYF; GYFFY; GYFYF |
| | AFFFF; AFYYF; AFFYF |
| | FAFFF |
| | YFAFF |
| BoNT/B | GFWGY; GFGWY; GAFFW; GFFFY; GFYFF |
| | AFYFF; AFFFY |
| | FFFFG |
| | YAYFF; YAFFY |
| BoNT/E | GFFGA; GWYFF |
| BotB complex | GFGFF; GYGFF; GFFYG; GFFGF |
| | AAGYY; AAAFF |
| RCA60 | GFYWF; GGFYY; GYYFY; GFYFF; GYFFY |
| | AFYAY; AFYYF |
| | WAFFF; WAFFF |
| RCA120 | GFFFA |
| | AYYYY |
| Cholera Toxin | FAWFF |
| | WAFWA |
| Protective Antigen (anthrax toxin) | YGYYA |
| | WFAFG |
| GS1-B4 lectin | AFYYF; AFFFA |
| | FWAFF; FAFFY |
| Human anti-αGal Antibody | GAWAY; FFWGY; FAWGA |
| Anti-Ley/H antibody | YYAYY |

Of the total sequences obtained, 90% contain three or four aromatic D-amino acids. Of those sequences identified from the G and A sublibraries (i.e., D-peptides with G or A residues at the amino-terminus), 89% contained three or four aromatic D-amino acids. One sequence, GFYFF, was identified as binding to ConA, BoNT/B and RCA60. Another sequence, GYFFY, was identified as binding to BoNT/A and RCA60. A third sequence, AFYYF, was identified as binding to RCA60, BoNT/A and GS1-B4. In two instances, the same sequence was identified as binding to a particular protein: GFFYF for BoNT/A and WAFFF for RCA60.

Sequences of Positive Beads from Binding Studies using TNFα and TGFβ1

TNFα and TGFβ1 obtained from commercial suppliers were incubated with the D-peptide library beads using the procedures described above and binding of the proteins detected using commercially available monoclonal and polyclonal antibody antibodies. Positive beads from the TNFα incubations with the F, Y and W sublibraries were removed and sequenced; positive beads from the incubation with TGFβ1 from the F sublibrary were removed and sequenced. The sequences are listed in Table 7.

TABLE 7

Sequences of D-peptides Binding TNFα or TGFβ1

| | |
|---|---|
| TNFα: | FFFAF; FFFAF |
| | YFAFF; YFAFF; YFAFF; YFAFF; YFYFA; YWAFF |
| | WGYAF; WGYFA; WAFFA |
| TGFβ1 | FFFGW; FWFGA; FYGYF; FWAAA; FAYYW; FGYYG; |
| | FWAWY; FFWYW; FAAFG; FYWAY; FYWGW; FAYFG; |
| | FYYYA; FWGFF; FFAWW |

The sequence YFAFF from the TNFα screen was found on four of the six Y sublibrary beads sequenced, and is the same sequence found as binding BoNT/A. Both beads sequenced from the F-sublibrary of the TNFα binding study had the identical sequence FFFAF. Two of the 27 total sequences (7%) contained two aromatic D-amino acids; six (22%) contained three aromatic D-amino acids; 17 (63%) contained four D-amino acids; and two (7%) contained five aromatic D-amino acids.

Microplate Assay to Determine Protein Binding to D-Peptide Sequences

Certain D-peptide sequences identified above as binding to proteins were synthesized with 3 or 4 D-lysine (K) residues at the carboxyl-terminus in order to increase solubility of the D-peptides in aqueous solutions. The D-lysine-containing D-peptides were covalently coupled to maleic anhydride-coated 96-well polystyrene plates (Pierce Chemical Co.) and the wells were backcoated. Coupling of the D-peptide occurs predominantly through the D-K amino groups and the majority of the D-peptides would then project from the walls of the plate into the solvent, mimicking the presentation of D-peptides on the TentaGel beads. Proteins were added to the D-peptide-coated wells at various concentrations and incubated for at least one hour to allow equilibrium of binding to occur. The wells were washed several times with PBS, and the relative amounts of protein bound were determined. Usually the proteins were biotinylated and the relative amounts of protein bound determined by adding AP-neutravidin and measuring bound AP by incubating with p-nitrophenyl-phosphate and measuring p-nitro-phenol calorimetrically. Maximum binding of proteins was established for the greater amounts of proteins added to the wells coated with particular D-peptides. Background binding for any protein was determined for wells not coated with D-peptide or wells lacking the protein incubation but with addition of the AP-neutravidin reagent. The dissociation equilibrium constant (Kd) could be estimated from the amount of protein added to the D-peptide coated wells that resulted in half maximal binding.

The D-peptides used to coat wells, the concentration of toxin at which saturation of binding was obtained, and the Kd estimates obtained for the proteins bound were as follows.

TABLE 8

Determination of Dissociation Constants for D-peptides Binding to Various Toxins

| D-peptide Sequences* used for Coating of Wells | Toxin Bound | Saturation Concentration, nM | Estimated Kd, nM |
|---|---|---|---|
| GFYFF, AFYAY or GFFFY | RCA60 | 100 | 20-25 |
| | BoNT/A or | 3-4 | 1-2 |
| GFGWY or GAFFW | BoNT/A or | 3-4 | 0.5-1 |
| GFFFY | BotB complex | 2.3 | 0.022 |

*The D-peptides used for coating the wells of the microplates each had three D-K residues added to the carboxyl-terminus for solubility and coating purposes.

The results indicate that the D-peptides have high binding affinities for the various toxins tested. It is of interest to note that the D-peptide sequence GFFFY, was identified as binding to the BoNT/B neurotoxin and the sequence in this binding assay bound both BoNT/B and BoNT/A neurotoxins as well as the BotB complex. The sequences GFGWY and GAFFW were also identified from D-peptide beads incubated with the BoNT/B neurotoxin and those D-peptides bound both the BoNT/A and BoNT/B neurotoxins. These results suggest that several of the D-peptide sequences will exhibit cross-reactivites to the structurally similar botulinum toxins, and that any one of such D-peptides, or mixture of D-peptides, may be useful for neutralizing the toxic effects of the several serotypes of the toxins and the Bot complex form of the toxin.

Test for Possible Toxicities of D-Peptides

Potential toxicities of D-peptides to be tested for the ability to neutralize toxins in animals was evaluated by injecting the D-peptides into mice intravenously (iv) or intraperitoneally (ip) and observing the animals over time for signs of toxicity.

TABLE 9

D-peptides Used in Toxicity Studies

| Experiment | Number Of mice | Route of injection | D-peptide(s)# | Amounts, ug | Concentrations*, mM |
|---|---|---|---|---|---|
| 1 | 5 | iv | GFWGY | 50 | 0.025 |
| 2 | 3 | ip | GFWGY | 250 | 0.125 |
| 3 | 2 | ip | GFYFF, AFYAY, WAFFF | 640 | 0.30 |
| 4 | 2 | ip | GFFYF, GYFFY | 430 | 0.21 |
| 5 | 3 | ip | GYFFF, GFFYF, | 973 | 0.46 |

The D-peptides used each had three D-lysine residues added to the carboxyl-terminus.
*The concentrations were calculated assuming a 2-ml blood volume for the mice.

In experiments 1 and 2, the mice exhibited no apparent toxicity (e.g., lethargy or ruffled fur) over a five day time period of observation. In experiments 3 and 4, the mice appeared to exhibit lethargy for the first 1 to 2 hours following administration of the D-peptides, and then exhibited no apparent signs of toxicity and appeared normal for the remainder of the three-day observation period. In experiment 5, the mice initially exhibited lethargy, ruffled fur and isolationism, then appeared normal on the following day of observation.

Prolongation of Survival of Mice Injected with Botulinum Toxin Plus D-Peptides

Experiment 1. Two groups of five mice each were injected ip with 500×$LD_{50}$ of BoNT/A neurotoxin alone or the same amount of neurotoxin plus a D-peptide mixture. The D-peptide mixture contained GYFFFKKK (263 µg), GFFYFKKK (500 µg), and GYFYFKKK (220 µg). Times to death for animals in each group were noted.

TABLE 10

Survival Times of Mice Injected with Toxin in the Presence or Absence of D-peptides.

| Animal number | Times to death in minutes | |
| --- | --- | --- |
| | BoNT/A group | BoNT/A plus D-peptides group |
| 1 | 140 | 193 |
| 2 | 142 | 260 |
| 3 | 191 | 290 |
| 4 | 198 | >300 |
| 5 | >300 | >300 |

The animals alive at >300 minutes were dead the following morning.

The mean survival times for the five animals given BoNT/A only was 194±29 (SEM) minutes (using 300 minutes for the one animal that survived for the initial five hours observation time). The mean survival time for the animals given BoNT/A plus the D-peptides was 269±20 minutes (using 300 minutes for the two mice that survived for the initial five hours of observation time). The p value for the differences in survival times between the two groups by the Students t test was 0.14; the p value using the chi square test was 0.11.

The mean survival times of mice given a large dose of BoNT/A (equivalent to 500× the $LD_{50}$ the toxin) and treated with D-peptides was increased by at least 35%, relative to untreated mice given the same dose of BoNT/A.

Experiment 2. Experiment 1 was repeated using the same amounts of BoNT/A neurotoxin (mice injected with 500× $LD_{50}$ of the toxin). The D-peptide mixture comprised GYFFFKKK (310 µg), GFFYFKKK (382 µg), and GYFYFKKK (310 µg) with the neurotoxin. Times to death for animals in each group were noted.

TABLE 11

Survival Times of Mice Injected with Toxin in the Presence or Absence of D-peptides.

| Animal number | Times to death in minutes | |
| --- | --- | --- |
| | BoNT/A group | BoNT/A plus D-peptides group |
| 1 | 117 | 193 |
| 2 | 121 | 231 |
| 3 | 137 | 309 |
| 4 | 138 | >330 |
| 5 | 165 | >330 |

Of the two mice that survived greater than the 330 minutes of initial observation time, one was dead the next morning and the other mouse survived.

The mean survival times of the animals given BoNT/A only was 135±8.5 (SEM) minutes. The mean survival times of the mice given BoNT/A plus D-peptides was 278±29 minutes (using 330 minutes as the survival times of the two mice that survived the initial 5.5 hour observation time). The p value for the difference in survival times was 0.01 using the Students t test and 0.009 using the chi square test.

The mean survival times of the group treated with BoNT/A and D-peptides was double that of the group treated with BoNT/A alone, and the differences were statistically significant.

I claim:

1. A combinatorial library consisting of multiple copies of D-peptides linked to supports so that the linked D-peptides are accessible for binding with proteins in a water based fluid phase added to the supports, wherein the length of each D-peptide is five D-amino acid residues, and wherein at least 68% of the D-peptides consist of at least three aromatic D-amino acid residues, and wherein the aromatic amino acid residues are selected from the group consisting of D-tryptophan, D-tyrosine, and D-phenylalanine, and the remaining amino acids are selected from the group consisting of glycine and D-alanine.

2. The combinatorial library of claim 1 wherein the supports consist of beads.

* * * * *